United States Patent
Conrad et al.

(10) Patent No.: US 9,661,805 B1
(45) Date of Patent: May 30, 2017

(54) SEED SOWING SYSTEM AND METHOD OF USE

(71) Applicant: BALL HORTICULTURAL COMPANY, West Chicago, IL (US)

(72) Inventors: Robert Scott Conrad, Wheaton, IL (US); Xiaolei Hu, Aurora, IL (US)

(73) Assignee: BALL HORTICULTURAL COMPANY, West Chicago, IL (US)

( * ) Notice: Subject to any disclaimer, the term of this patent is extended or adjusted under 35 U.S.C. 154(b) by 0 days.

(21) Appl. No.: 14/983,110

(22) Filed: Dec. 29, 2015

(51) Int. Cl.
| | |
|---|---|
| *G01N 21/55* | (2014.01) |
| *A01G 9/08* | (2006.01) |
| *G01V 8/12* | (2006.01) |
| *A01C 7/08* | (2006.01) |
| *G01N 21/552* | (2014.01) |

(52) U.S. Cl.
CPC .............. *A01G 9/085* (2013.01); *A01C 7/084* (2013.01); *G01N 21/553* (2013.01); *G01V 8/12* (2013.01)

(58) Field of Classification Search
CPC ................................................ G01N 33/56961
See application file for complete search history.

(56) References Cited

U.S. PATENT DOCUMENTS

| | | | |
|---|---|---|---|
| 3,927,400 A | 12/1975 | Knepler | |
| 4,009,799 A | 3/1977 | Fathauer | |
| 4,085,862 A | 4/1978 | Steffen | |
| 4,159,064 A | 6/1979 | Hood | |
| 4,277,833 A | 7/1981 | Steffen | |
| 4,333,096 A | 6/1982 | Jenkins et al. | |
| 4,369,895 A | 1/1983 | McCarty et al. | |
| 4,616,577 A * | 10/1986 | van der Lely | A01C 7/105 111/178 |
| 4,635,214 A | 1/1987 | Kasai et al. | |
| 4,635,215 A | 1/1987 | Friend | |
| 4,675,520 A | 6/1987 | Harrsen et al. | |
| 5,025,951 A | 6/1991 | Hook et al. | |
| 5,323,721 A | 6/1994 | Tofte et al. | |
| 5,635,911 A | 6/1997 | Landers et al. | |
| 5,847,389 A | 12/1998 | Mertins et al. | |

(Continued)

FOREIGN PATENT DOCUMENTS

| | | |
|---|---|---|
| CN | 202050677 U | 11/2011 |
| EP | 1566089 A1 | 8/2005 |

(Continued)

*Primary Examiner* — Michael P Stafira
(74) *Attorney, Agent, or Firm* — Marshall, Gerstein & Borun LLP; Randall G. Rueth

(57) ABSTRACT

A seed sowing system for depositing seeds in a germination tray is disclosed. The seed sowing system may include a rotatable drum having a plurality of rows of apertures configured to pick up, carry, and release the seeds so that they fall into respective depressions in the germination tray. A light source may be provided to illuminate the row of seeds as each row passes through an illumination region while being carried on the rotatable drum. A detector may be positioned to capture light reflected from the rows of seeds as each row passes through the illumination region. Output signals from the detector may be analyzed to determine an improper quantity of seeds at predetermined locations on the rotatable drum. Based on this analysis, an alert and/or report may be provided to the operator so that he or she can adjust and/or repair the seed sowing system.

19 Claims, 4 Drawing Sheets

(56) References Cited

U.S. PATENT DOCUMENTS

| | | | |
|---|---|---|---|
| 5,924,371 A | 7/1999 | Flamme et al. | |
| 5,936,234 A | 8/1999 | Thomas et al. | |
| 5,956,255 A | 9/1999 | Flamme | |
| 5,969,340 A | 10/1999 | Dragne et al. | |
| 6,024,035 A | 2/2000 | Flamme | |
| 6,070,538 A | 6/2000 | Flamme et al. | |
| 6,070,539 A | 6/2000 | Flamme et al. | |
| 6,078,635 A | 6/2000 | DuBois | |
| 6,091,997 A | 7/2000 | Flamme et al. | |
| 6,093,926 A | 7/2000 | Mertins et al. | |
| 7,478,603 B2 | 1/2009 | Riewerts et al. | |
| 8,365,679 B2 | 2/2013 | Landphair et al. | |
| 8,631,749 B2 | 1/2014 | Sauder et al. | |
| 8,868,300 B2 | 10/2014 | Kocer et al. | |
| 8,942,896 B2 | 1/2015 | Mayerle | |
| 2006/0011647 A1 | 1/2006 | Sauder et al. | |
| 2007/0266917 A1 | 11/2007 | Riewerts et al. | |
| 2009/0032441 A1* | 2/2009 | Corak | B07C 5/3425 209/3.3 |
| 2010/0143906 A1* | 6/2010 | Becker | B07C 5/3425 435/6.13 |
| 2014/0076216 A1 | 3/2014 | Kormann et al. | |
| 2014/0191857 A1 | 7/2014 | Sauder et al. | |
| 2015/0066932 A1 | 3/2015 | Stuber et al. | |

FOREIGN PATENT DOCUMENTS

| | | |
|---|---|---|
| EP | 1932413 A1 | 6/2008 |
| WO | WO-2008135722 A1 | 11/2008 |
| WO | WO-2015106079 A1 | 7/2015 |

\* cited by examiner

SEED SOWING SYSTEM AND METHOD OF USE

FIELD OF THE DISCLOSURE

The present disclosure generally relates to seed sowing systems and, more particularly, to seed sowing systems capable of transferring seeds from a hopper or other reservoir to a germination tray.

BACKGROUND

Sowing seeds typically involves depositing seeds at predetermined, regular intervals so that the plants grown from the seeds are distributed in a pattern that facilitates watering, fertilizing, harvesting, sunlight exposure, and other agricultural functions. Many plants are initially grown in a germination tray before being transplanted into the ground or another container. Germination trays are typically flat and have a plurality of depressions arranged in a number of evenly-spaced rows and/or columns. Typically each of the depressions is filled with soil and sowed with a single seed so that each of the depressions yields a single seedling.

Manually planting seeds in a germination tray can be a labor-intensive and time-consuming process. Therefore, many growers employ a seed sowing machine to automatically plant the seeds in the germination tray. One conventional type of seed sowing machine is a drum seeder which includes a rotating drum configured to transfer seeds from a hopper or other reservoir into the depressions of the germination tray. Typically the rotating drum has a plurality of apertures that provide suction to pick up the seeds so that they can be carried away from the hopper on the exterior of the rotating drum. Once a seed is aligned above a depression in the germination tray, the suction force holding the seed to the rotating drum is removed and the seed is dropped into the depression. Meanwhile, the germination tray is conveyed beneath the rotating drum, so that the next depression receives the next seed dropped from the rotating drum.

The yield of seedlings is dependent on the drum seeder depositing a single seed, or a desired quantity of seeds, in each of the depressions in the germination tray. If the drum seeder misses one or more depressions, or deposits an excess number of seeds in one or more of the depressions, it may have a negative impact on the yield of seedlings. Also, since it may be difficult and/or cost-prohibitive for a grower to manually inspect each of the depressions for a missing seed and/or multiple seeds, the grower may be unaware that the drum seeder is malfunctioning, or has suboptimal settings, until the seedlings begin to sprout from the germination tray.

A variety of factors can cause the drum seeder to deliver an improper amount of seeds. Such factors include clogged apertures, improper machine settings (e.g., rotational speed of the drum, vacuum pressure level, etc.), characteristics of the seeds (e.g., size, shape, etc.), and other factors. Knowledge of which of these factors is reducing the yield of seedlings can be useful to a grower so that the grower can adjust and/or fix the drum seeder. Conventional drum seeders, however, usually do not provide the grower with diagnostic information, especially not the kind needed to ascertain the cause of a low yield of seedlings.

The present disclosure sets forth seed sowing systems and methods of sowing seeds embodying advantageous alternatives to existing seed sowing systems and methods of sowing seeds, and that may address one or more of the challenges or needs mentioned above, as well as provide other benefits and advantages.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. Also, none of the drawings are necessarily to scale.

SUMMARY

Figure 1:
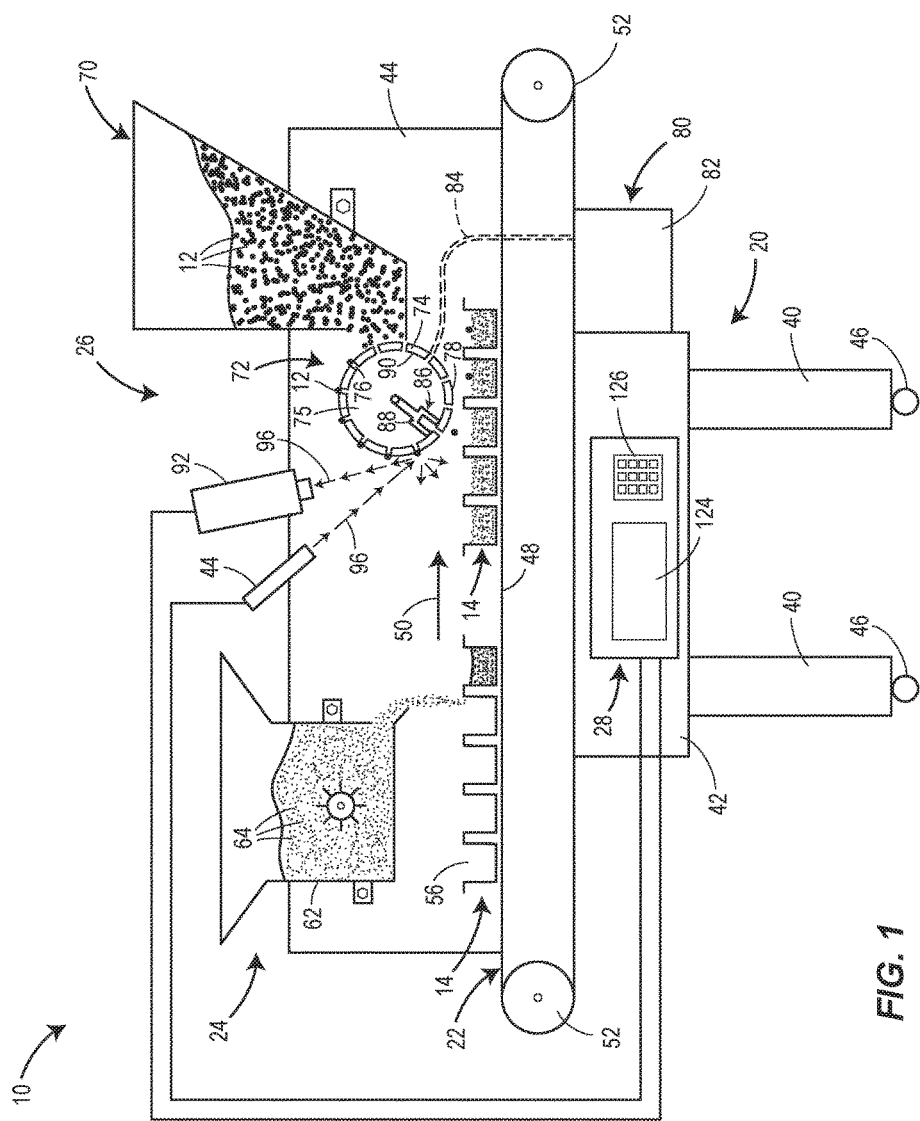
FIG. 1 is a schematic representation of one embodiment of a seed sowing system constructed in accordance with principles of the present disclosure.

Disclosed herein is a seed sowing system for depositing seeds in a germination tray. The system may include a frame, a drum rotatably connected to the frame, a hopper connected to the frame, a vacuum, a light source, and an optical detector. The drum may be rotatable about a longitudinal axis and have an cylindrical peripheral wall and a hollow interior. A plurality of rows of apertures may be formed in the cylindrical peripheral wall and may be in fluid communication with the hollow interior. Each row of the plurality of rows of apertures may be parallel to the longitudinal axis. The hopper may be configured to deliver seeds onto the cylindrical peripheral wall during operation. The vacuum may be configured to reduce pressure within the hollow interior of the drum so that the seeds from the hopper are temporarily held against the cylindrical peripheral wall at the plurality of rows of apertures in a plurality of rows of seeds. The light source may be configured to illuminate the plurality of rows of seeds one at a time as each row passes through an illumination region during operation. The optical detector may be positioned to receive light reflected by the plurality of rows of seeds when each row passes through the illumination region.

Also disclosed is a seed monitoring system including a rotatable drum, a directional light source, and a detector. The rotatable drum may have a cylindrical peripheral wall formed with a plurality of apertures. The plurality of apertures may be configured to hold seeds against temporarily the cylindrical peripheral wall with suction. The directional light source may be configured to emit rays of light offset from the cylindrical peripheral wall so that the rays of light pass through an illumination region adjacent to the cylindrical peripheral wall. The detector may be positioned to receive the rays of light reflected by at least one of the seeds held on the cylindrical peripheral wall when the at least one of the seeds passes through the illumination region during rotation of the rotatable drum.

Further disclosed is method of monitoring seeds within a seed sowing system. The seed sowing system may have a rotatable drum rotatable about a longitudinal axis, a directional light source, a detector, a processor, and a plurality of apertures formed in the rotatable drum. The plurality of apertures may be configured to pick up, carry, and release the seeds. The method may include: (a) providing a laser to emit rays of light perpendicular to the longitudinal axis of the rotatable drum and offset from a cylindrical peripheral wall of the rotatable drum; (b) providing an optical detector to receive the rays of light reflected by the seeds carried by the rotatable drum; (c) transmitting seed signals to the processor based on the rays of light received by the optical detector; and (d) processing the seed signals with the processor to determine a condition of at least one of the plurality of apertures.

DETAILED DESCRIPTION

The present disclosure is generally directed to a seed sowing system capable of detecting and reporting anomalies in its distribution of seeds. The seed sowing system may include a light source configured to illuminate seeds carried on a rotatable drum and a detector positioned to capture the light reflected by the seeds as well as output signals representative of the presence of seeds. The light source may be configured so that it illuminates rows of seeds on the rotatable drum one at a time as each row passes through an illumination region. So configured, the detector may receive bursts of reflected light which are brighter than ambient lighting conditions when each row of seeds passes through the illumination region. As such, fluctuations in ambient lighting conditions may be less likely to influence the seed detection capabilities of the detector. Furthermore, the seed sowing system of the present disclosure may be configured to alert an operator when there is an absence of seeds, or an excess number of seeds, carried on the rotatable drum, and/or provide the operator with diagnostic information so that the grower can more accurately predict a yield of seedlings and/or identify the cause of improper seed delivery.

Each of the foregoing components of the seed sowing system and methods of operating the seed sowing system will now be described in more detail.

Referring to FIG. 1, illustrated is a schematic representation of one embodiment of a seed sowing system 10 which can be used to plant seeds 12 in a germination tray 14 in accordance with principles of the present disclosure. The seed sowing system 10 may include a frame 20, a conveyor 22, a soil dispensing station 24, a seed dispensing station 26, and a computing device 28. Additional upstream and/or downstream stations may be added to the seed sowing system 10 such as, for example, a watering station, a tray stacking station, among others. Furthermore, the stations of the seed sowing system 10 may be modular such that the stations can be arranged in various combinations and/or set up to accommodate various floor arrangements.

The frame 20 may be composed of a plurality of rigid support elements such as vertical leg members 40, a control panel 42, and one or more mounting structures 44 configured to suspend the soil and seed dispensing elements, and other components, above the conveyor 22. The vertical leg members 40 may be mounted on wheels 46 so that the seed sowing system 10 can be rolled by an operator between different locations.

The conveyor 22 may include a continuous belt 48 configured to move the germination trays 14 in a conveying direction 50 relative to the soil dispensing station 24 and/or the seed dispensing station 26. The continuous belt 48 may be wrapped around a plurality of rollers 52, at least one of which may be rotated by a motor (not illustrated). The rollers 52 may be rotatably connected to the frame 20.

Figure 2:
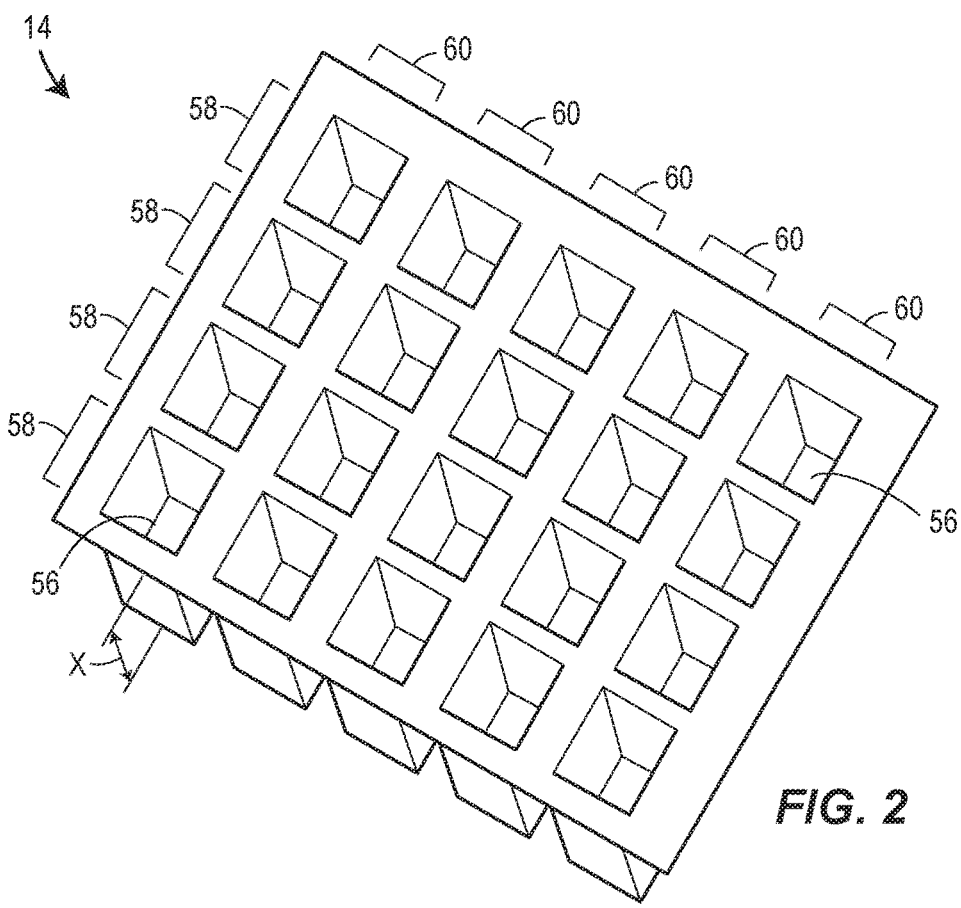
FIG. 2 is a top perspective view of one embodiment of a germination tray constructed in accordance with principles of the present disclosure.

As illustrated in FIG. 2, the germination tray 14 includes a planar upper surface 54 in which a plurality of depressions 56 are formed. The depressions 56 may be arranged in a plurality of evenly-spaced rows 58 and columns 60. When placed on the conveyor 22, the rows 58 of the germination tray 14 may be arranged so that they are substantially parallel to the conveying direction 50 of the conveyor 22. In some embodiments, the depressions 56 may be squared-shaped when viewed from above, and have sides measuring approximately (e.g., ±10%) two inches across, and a depth X of approximately (e.g., ±10%) three inches. Also, in some embodiments, the germination tray 14 may be made of a lightweight, semi-rigid material such as plastic.

Referring back to FIG. 1, the soil dispensing station 24 may include a soil hopper 62 fixedly connected to the frame 20 and filled with soil 64. The soil hopper 62 may have an exit port 66 at its bottom through which a quantity of the soil 64 can be dispensed. Additionally, the soil hopper 62 may house a rotatable drum 68 having a plurality of radial agitators 70 (e.g., fins, grooves, etc.) configured to move the soil 64 toward the exit port 66 at a controlled rate. The rotational speed of the rotatable drum 68 may be set by the operator via the computing device 28. As shown in FIG. 1, the soil hopper 62 may be mounted above the conveyor 22 so that the soil 64 dispensed from its exit port 66 falls into the depressions 56 of the germination tray 14 as the germination tray 14 moves in the conveying direction 50.

Figure 3:
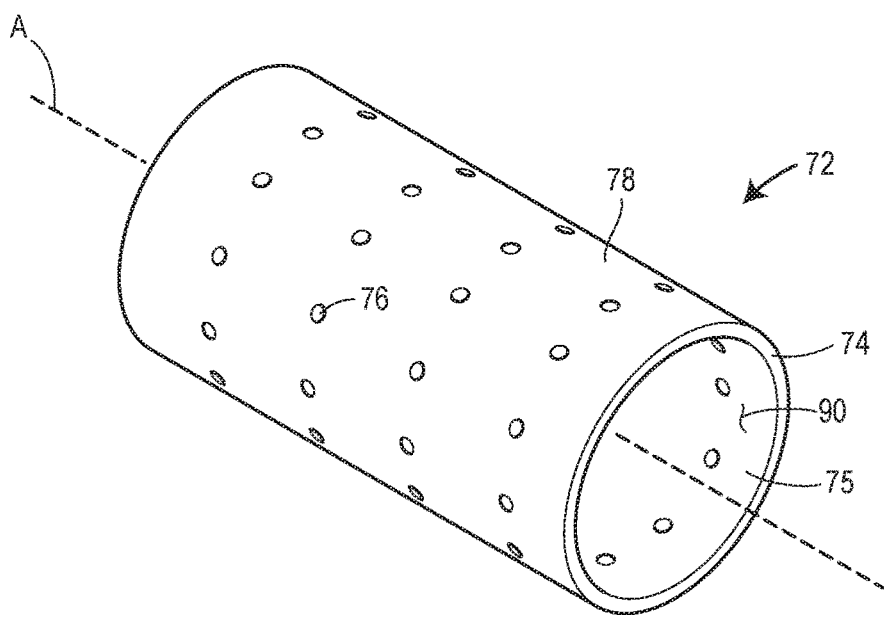
FIG. 3 is a side perspective view of one embodiment of a rotatable drum of a seed dispensing station constructed in accordance with principles of the present disclosure.
Figure 4:
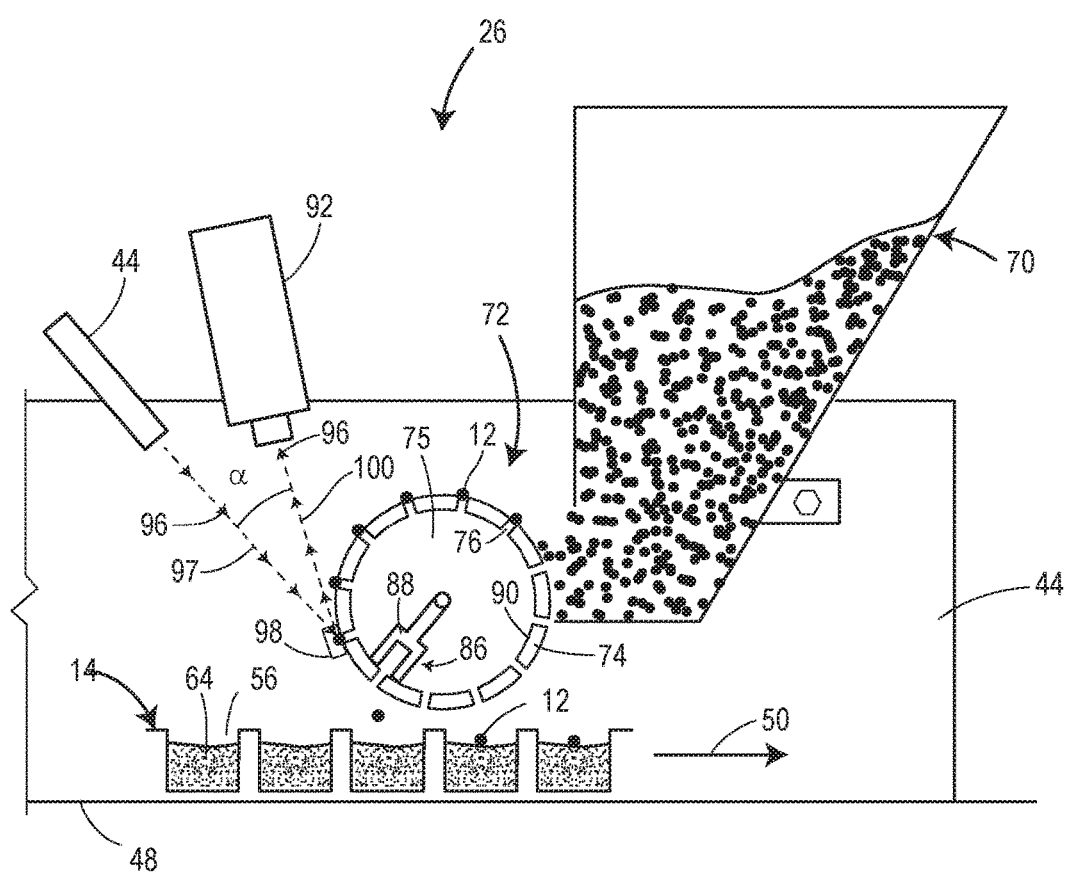
FIG. 4 is enlarged, schematic view of the seed dispensing station illustrated in FIG. 1.

Still referring to FIG. 1, the seed dispensing station 26 may include a seed hopper 70 fixedly connected to the frame 20 and filled with the seeds 12. The seed hopper 70 may have an exit port 66 at its bottom through which a quantity of the seeds 12 can be dispensed. The seed dispensing station 26 may further include a rotatable drum 72 rotatably connected to the frame 20 and disposed immediately adjacent to the exit port 66 of the seed hopper 70. As seen in FIG. 3, the rotatable drum 72 may be rotatable about its longitudinal axis A, which extends along the length of the rotatable drum 72. The rotatable drum 72 may be rotated by an electric motor (not illustrated) whose speed is controllable by the computing device 28. In FIGS. 1 and 4, the rotatable drum 72 is configured to rotate in the counter-clockwise direction during operation.

Furthermore, the rotatable drum 72 may include a cylindrical peripheral wall 74 that surrounds and defines a hollow interior 75. A plurality of apertures 76 (e.g., through holes) may extend through the cylindrical peripheral wall 74 so that they are in fluid communication with the hollow interior 75 of the rotatable drum 72. The apertures 76 may be arranged in a plurality of circumferential and longitudinal rows which are evenly spaced longitudinally and circumferentially, respectively, over an exterior surface 78 of the cylindrical peripheral wall 74. Each of the longitudinal rows may be parallel to the longitudinal axis A of the rotatable drum 72. Each of the apertures 76 may have a circular cross-section and a diameter which is smaller than that of a largest dimension of each of the seeds 12. Therefore, in some embodiments, the seeds 12 cannot be sucked through the apertures 76. In some embodiments, a hemispherical dimple (not illustrated) may be formed in the exterior surface 78 of the cylindrical peripheral wall 74 at each of the apertures 76, thereby providing a seat for one of the seeds 12. As described in more detail below, each of the apertures 76 is intended to provide suction which temporarily holds a single seed 12 against the exterior surface 78 of the cylindrical peripheral wall 74 so that each longitudinal row of apertures 76 provides a longitudinal row of the seeds 12.

The seed dispensing station 26 may further include a vacuum assembly 80 including a vacuum pump 82 in fluid communication with the hollow interior 75 of the rotatable drum 72 by virtue of a hose 84 or other conduit. The vacuum pump 82 may be configured to reduce the air pressure within the hollow interior 75 so that it is lower than atmospheric pressure. As such, suction may be created through the apertures 76. This suction may cause each longitudinal row of the apertures 76 to pick up a longitudinal row of the seeds 12 as the longitudinal row of apertures 76 passes the exit port 66 of the seed hopper 70. Since the seeds 12 may be larger than the apertures 76, the seeds 12 are held by the suction force against the exterior surface 78 of the cylindrical peripheral wall 74 while the rotatable drum 72 rotates. In some embodiments, the vacuum pump 82 may be controllable by the computing device 28 so that an operator can set a desire pressure level within the hollow interior 75.

To release the seeds 12 from the rotatable drum 72, the seed dispensing station 26 may include a seed dislodging unit 86. In some embodiments, such as the one illustrated in FIGS. 1 and 4, the seed dislodging unit 86 may be disposed within the hollow interior 75 and take the form of a pressure shoe 88 that slidably engages an inner surface 90 of the peripheral cylindrical wall 74. The pressure shoe 88 may configured to create a positive pressure at the inner side of one of the longitudinal rows of the apertures 76 in the lower half of the rotating drum. Accordingly, this longitudinal row of the apertures 76 may release its seeds 12 so that they are dropped into respective depressions 56 in the germination tray 14. The positive pressure created by pressure shoe 88 need only be positive relative to the pressure level within the hollow interior 75. Thus, in some embodiments, the pressure shoe 88 may only need to create a pressure at the inner side of a longitudinal row of the apertures 76 that is equal to atmospheric pressure in order to release a longitudinal row of the seeds 12.

Referring to FIG. 4, the seed dispensing station 26 may have a seed monitoring system 90 including at least an optical detector 92 and a directional light source 94. Each of the optical detector 92 and the directional light source 94 may be fixedly connected to the frame 20, but still allow for of slight manual adjustments of their orientation. The directional light source 94 may be configured to emit rays of light 96 that pass through an illumination region 98 immediately adjacent to, but not overlapping, a portion of the rotatable drum 72 which carries the seeds 12. In some embodiments, all of or a substantial portion of the rays of light 96 emitted from the directional light source 94 may travel along an optical emission path 97 extending linearly from the directional light source 94, so that a peak intensity of the directional light source 94 is aligned along the optical emission path 97. As illustrated in FIG. 4, the rays of light 96 emitted by the directional light source 94 (as well as the optical emission path 97 of the directional light source 94) may be perpendicular to the longitudinal axis A of the rotatable drum 72 and offset from the exterior surface 78 of the cylindrical peripheral wall 74 of the rotatable drum 72 by a distance Y. In some embodiments, the distance Y may be less than or equal to an average diameter, or an average greatest outer dimension, of each of the seeds 12. Accordingly, the rays of light 96 strike and are reflected (e.g., diffusely reflected or specularly reflected) by the seeds 12 when the seeds 12 pass through the illumination region 98 while being carried on the rotatable drum 72. In some embodiments, none or a negligible amount of the rays of light 96 may strike the exterior surface 78 of the cylindrical peripheral wall 74 of the rotatable drum 72, so that few or none of the rays of light 96 are reflected by the exterior surface 78 toward the optical detector 92. Also, in some embodiments, the rays of light 96 (as well as the optical emission path 97) may be parallel to and offset from an imaginary line which is tangential to the exterior surface 78 of the cylindrical peripheral wall 74 of the rotatable drum 72, wherein the imaginary line touches at least one of the apertures 76 when the aperture 76 is aligned with the illumination region 98. In some embodiments, the rays of light 96 (as well as the optical emission path 97) may be offset from this imaginary tangential line by a distance in a range between approximately (e.g., ±10%) 0-3.0 mm, or 0-2.0 mm, or 0-1.0 mm, or 0.5-1.5 mm, or 0.5-1.0 mm, or any other suitable range based on the average diameter or height of the seeds.

As a result of the arrangement of the rays of light 96 relative to the cylindrical peripheral wall 74, the directional light source 94 may illuminate the longitudinal rows of the seeds 12 one at a time as each longitudinal row of the seeds 12 rotates through the illumination region 98. In order to illuminate an entire longitudinal row of the seeds 12, the directional light source 94 may include a lens (not illustrated) that distributes the rays of light 96 across a plane aligned with the optical emission path 97. Also, in some embodiments, the directional light source 94 may be a laser that emits a single wavelength of light or a narrow range of wavelengths of light.

At least a portion of the rays of light 96 reflected by the seeds 12 may be directed along an optical detection path 100 of the optical detector 92. The optical detection path 100 may correspond to a centerline of a field of view of the optical detector 92 and/or an imaginary line along which the optical detector 92 has a peak spectral sensitivity. Furthermore, the optical detection path 100 may intersect the illumination region 98. The portion of the rays of light 96 which are reflected by the seeds 12 along the optical detection path 100 are received by the optical detector 92. In turn, the optical detector 92 may convert the received rays of light 96 into seed signals (e.g., electric signals) which may be transmitted to the computing device 28 for processing. The optical detectors 92 may be configured to transmit the seed signals to the computing device 28 via a wired connection as illustrated in FIG. 1, or alternatively, via a wireless connection.

The optical detector 92 may incorporate a charge-coupled device (CCD), a complementary metal-oxide-semiconductor (CMOS), a photodiode, a photoresistor, a photovoltaic cell, or any other suitable photodetector capable converting the light reflected by the seeds 12 into electric signals. In some embodiments, the optical detector 92 may be a digital camera (e.g., a line scan camera). Furthermore, in some embodiments, the peak spectral sensitivity of the optical detector 92 may correspond to a wavelength, or a range of wavelengths, of light emitted by the directional light source 94. Accordingly, the optical detector 92 may be most sensitive to the light emitted by the directional light source 94, thus making it less susceptible to changes in ambient lighting conditions.

Still referring to FIG. 4, the optical emission path 97 of the directional light source 94 (and thus the rays of light 96 emitted by the directional light source 94) may be oriented at an angle α relative to the optical detection path 100 of the optical detector 92. In some embodiments, the angle α may be any angle equal to a greater than approximately (e.g., ±10%) 5 degrees. In other embodiments, the angle α may be within a range of approximately (e.g., ±10%) 5-90 degrees, or 5-75 degrees, or 5-60 degrees, or 5-60 degrees, or 5-45 degrees, or 5-30 degrees, or 5-20 degrees, or 5-15 degrees, or 5-10 degrees.

The longitudinal rows of the seeds 12 carried on the rotatable drum 72 reflect the rays of light 72 to the optical detector 92 only when they momentarily pass through the illumination region 98. Thus, the optical detector 92 receives intermittent bursts of reflected light from the longitudinal rows of the seeds 12. These bursts of light may be significantly brighter than ambient lighting conditions and the optical detector 92 may be calibrated to detect these bursts of light. As such, the optical detector 92 may be less likely to make improper measurements as the result of fluctuations in ambient lighting conditions.

In some embodiments, the seeds may be coated with a substance that improves their reflective properties, thereby increasing the signal to noise ratio when a seed is present in the optical detection path 100. Such coatings include, but are not limited to, fluorescent dyes capable of excitation and ground plant tissues including chlorophyll capable of excitation.

As shown in FIGS. 1 and 4, the seed dispensing station 26 may also include an encoder 110 configured to output position signals to the computing device 28 indicative of the current rotational position of the rotatable drum 72. The computing device 28 may only process seed signals received by the optical detector 92 when the rotational position of the rotatable drum 72 corresponds to one of the longitudinal rows of the seeds 12 passing through the illumination region 98. As such, the data processing and/or storage burden on the computing device 28 may be reduced. In alternative embodiments, the encoder 110 may be omitted, and the computing device 28 may process all of the seed signals it receives from the optical detector 92.

Figure 5:
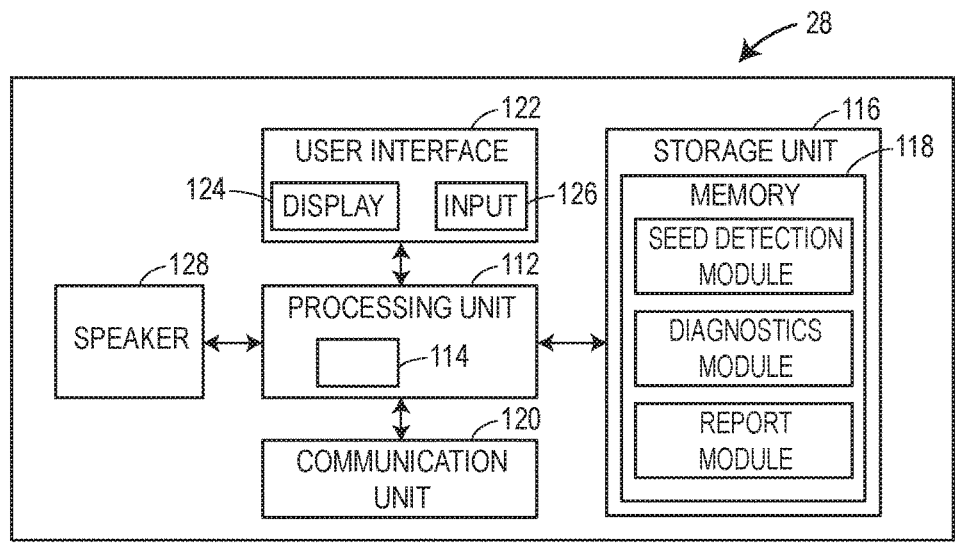
FIG. 5 is block diagram of one embodiment of a computing device constructed in accordance with principles of the present disclosure.

Turning to FIG. 5, the computing device 28 may include a processing unit 112 having one or more processors 114 (e.g., microprocessors), a storage unit 116 having one or more tangible, non-transitory computer-readable memories 118 (e.g., a RAM, a non-volatile memory such as a hard disk, a flash memory, a removable memory, a non-removable memory, etc.), a communication unit 120, a user interface 122 having a display 124 (e.g., a touchscreen, a computer monitor, a liquid crystal display, etc.) and an input unit 126 (e.g., a physical keyboard, touchscreen keyboard, button, etc.), and a speaker 128. In at least one embodiment, a touchscreen may form both the display 124 and the input unit 126. The components of the computing device 28 may communicate directly with each other via a system bus (not illustrated). The processing unit 112 may be configured to fetch and execute instructions stored in the storage unit 116 to control the operation of, for example, the communication unit 120, the user interface 122, the speaker 128, and/or other components of the computing device 28 not illustrated in FIG. 5. The communication unit 120 may be configured to receive the seed signals from the optical detector 92 and the position signals from the encoder 110, and other signals from other components and sensors of the seed sowing system 10. Furthermore, the communication unit 120 may be configured to transmit signals to various components of the seed sowing system 10 to control their operation (e.g., the communication unit 120 may transmit speed control signals to the motor responsible for driving the rotatable drum 72).

In some embodiments, the memory 118 of the storage unit 116 may store a seed detection module 130, a diagnostic module 132, and a report module 134. The seed detection module 130 may be configured to process the seed signals received from the optical detector 92 to determine a condition of each of the apertures 76 each time each of the apertures 76 rotates past the illumination region 98. In some embodiments, the seed detection module 130 may utilize an image processing algorithm to determine one of the following conditions for each of the apertures 76: (a) a presence of a single seed, (b) an absence of seeds, or (c) a presence of two or more seeds. The seed detection module 130 may process only those seed signals received from the optical detector 92 when the position signal received from the encoder 110 indicates that the rotational positional of the rotatable drum 72 corresponds with one of the longitudinal rows of apertures 76 being aligned with the illumination region 98. If the seed detection module 130 detects an absence of seeds and/or a presence of two or more seeds at one of the apertures 76, the seed detection module 130 may output an error signal to the diagnostic module 132 and/or the report module 134. The seed detection module 130 may repeatedly perform its determination of the condition of the apertures 76 each time a longitudinal row of the apertures 76 rotates past the illumination region 98.

In some embodiments, the seed detection module 130 may be configured to process the seed signals to determine the height of the object on the rotatable drum 72 which has reflected the rays of light 96 toward the optical detector 92. This determination may be accomplished through triangulation (e.g., trigonometric) methods. The seed detection module 130 may compare the height with a predetermined value to determine if the object on the rotatable drum 72 is a single seed, multiple seeds, and/or a non-seed object. For example, if the minimum diameter or height of each of the seeds is 1.0 mm, the seed detection module 130 may determine that a seed is present on the rotatable drum 72 when the height calculated by the seed detection module 130 is greater than 1.0 mm.

The diagnostic module 132 may be configured to measure the time between the error signals output from the seed detection module 130 to determine the regularity of the error signals on a per aperture basis. If the error signals occur regularly or periodically (i.e., an equal amount of time exists between each of the error signals), the diagnostic module 132 may determine that the cause of the error signals is related to a malfunctioning component (e.g., a clogged aperture). If the error signals occur randomly or irregularly (i.e., a different amount of time exists between each of the error signals), the diagnostic module 132 may determine that the cause of the error signals is related to an improper component setting (e.g., a speed of the rotational drum 72 is set too high, a vacuum level of the vacuum pump 82 is set too high, etc.). Furthermore, the diagnostic module 132 may be configured to count the total number of error signals, on a per aperture basis, received during an operator-defined defined time period. Based on the total number of error signals, the diagnostic module 132 may be configured to project the yield of seedlings (e.g., the percentage of the depressions in the germination tray(s) that will grow a seedling).

The report module 134 may be configured to generate a notification for communicating the information generated by the diagnostic module 132 to the operator. The notification may take any suitable form including an alarm emitted through the speaker 128, and/or text and/or graphics displayed through the display 124. In some embodiments, the notification may include a chart summarizing diagnostic information from an operator-defined time period including, for example, the number skips (i.e., the number of error signals associated with "absence of seed" detections), the number of multiple or excess seed deliveries (i.e., the number of error signals associated with "two or more seeds" detections), the projected yield of seedlings, and/or indication of the cause or source of the error signals.

Figure 6:
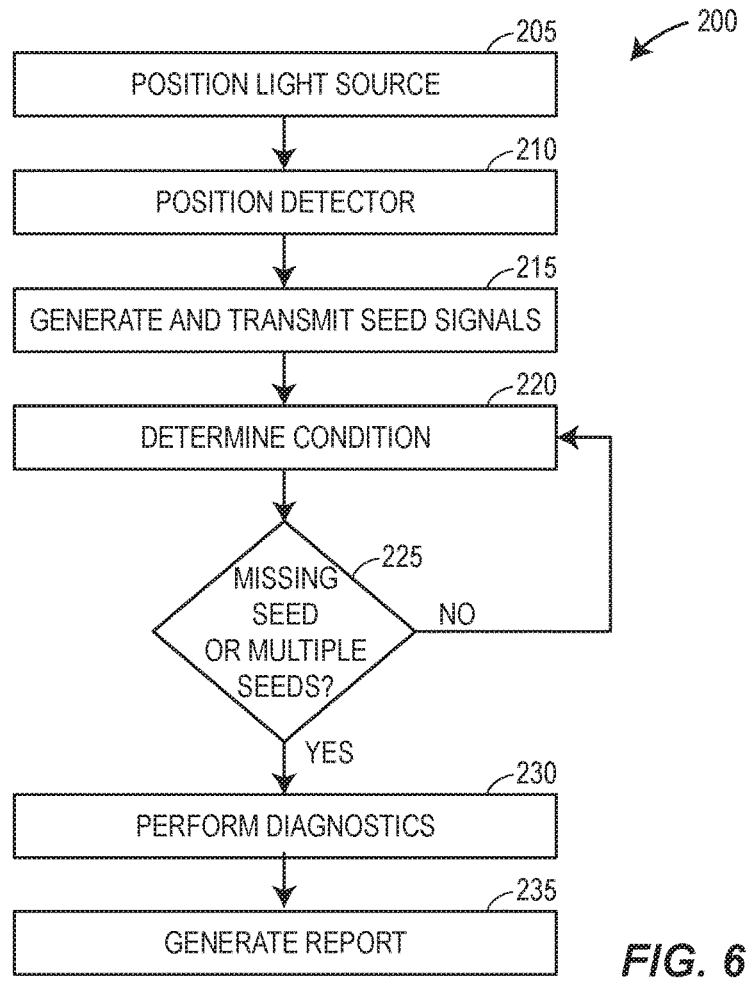
FIG. 6 is a flowchart of one embodiment of a method of sowing seeds according to principles of the present disclosure.

Turning to FIG. 6, illustrated is a flow diagram of an exemplary method 200 of monitoring seeds within a seed sowing system such as the one described above. One or more steps of the method 200 may be saved, in whole or in part, as a set of instructions, routines, programs, modules, and/or applications on one or more memories, such as the memory 118.

The method 200 may begin with an operator orienting the directional light source 94 so that its optical emission path 97, as well as the rays of light 96 the directional light source 94 will emit during operation, are offset from the exterior surface 78 of the cylindrical peripheral wall 74 of the rotatable drum 72 and perpendicular to the longitudinal axis A of the rotatable drum 72 (block 205). Next, the operator may orient the optical detector 92 so that it will receive the rays of light 96 reflected by the seeds 12 carried on the rotatable drum 72 during operation (block 210). This step may involve the operator orienting the optical detector 92 so that its optical detection path 100 is arranged at the angle α relative to the optical emission path 97 of the directional light source 94. In some embodiments, the steps of orienting the directional light source 94 and the optical detector 92 may be preceded by the operator outfitting an existing seed sowing system with the directional source 94 and the optical detector 92.

Once the directional light source 94 and the optical detector 92 have been properly oriented, the operator may begin using the seed sowing system 10 to deposit the seeds 12 in respective depressions 56 of the seed germination tray 14. During operation, the optical detector 92 may transmit seed signals to the computing unit 28 based on the rays of light 96 reflected by the seeds 12 passing through the illumination region 98 (block 215). In response to receiving the seed signals, the processing unit 112 may execute the seed detection module 130 to process the seed signals to determine a condition of each of the apertures 76 (block 220). The condition determined by the seed detection module 130 for each aperture 76 may indicate whether the apertures 76 carries a single seed, no seeds, or multiple or excess seeds (block 225). In the event of a missing seed condition or a multiple or excess seed condition, the seed detection module 130 may output an error signal, and the processing unit 112 may subsequently execute the diagnostic module 132 (block 230). The diagnostic module 132 may analyze the error signals received over an operator-defined period of time to extrapolate various diagnostic information such as the regularity of the error signals and the projected yield of seedlings, as discussed above in more detail. Subsequently, the processing unit 112 may execute the report module 134 to process the diagnostic information, which may result in the report module 134 controlling the speaker 128 to emit an audio alarm and/or controlling the display 124 to display the a summary of the diagnostic information (block 235).

While the seed sowing system 10 of the present embodiment is generally disclosed as being a stationary machine that delivers seeds to a germination tray conveyed therethrough, the scope of the present disclosure is not limited to this configuration. Rather, alternative embodiments of the seed sowing system 10 can be configured as movable, trailer-like machine which can be towed by a tractor or other vehicle over a ground surface and which deposits seeds in the ground surface.

From the foregoing, it can be seen that the present disclosure advantageously provides a seed sowing system which can more accurately detect anomalies in the quantity of seeds delivered. The seed sowing system may employ a seed monitoring system which is not reliant on ambient light and thus less susceptible to fluctuations in ambient lighting conditions. Additionally, the seed sowing system is configured to provide an operator with diagnostic information to help the operator identify the cause of improper seed delivery.

Additional Considerations

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain implementations are described herein as including logic or a number of components, modules, or mechanisms. Modules may constitute either software modules (e.g., code implemented on a tangible, non-transitory machine-readable medium such as RAM, ROM, flash memory of a computer, hard disk drive, optical disk drive, tape drive, etc.) or hardware modules (e.g., an integrated circuit, an application-specific integrated circuit (ASIC), a field programmable logic array (FPLA)/field-programmable gate array (FPGA), etc.). A hardware module is a tangible unit capable of performing certain operations and may be configured or arranged in a certain manner. In exemplary implementations, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein, the terms "comprises," "comprising," "includes," "including," "has," "having" or any other variation thereof, are intended to cover a non-exclusive inclusion.

For example, a process, method, article, or apparatus that comprises a list of elements is not necessarily limited to only those elements but may include other elements not expressly listed or inherent to such process, method, article, or apparatus.

In addition, use of the "a" or "an" are employed to describe elements and components of the implementations herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a method for sowing seeds through the disclosed principles herein. Thus, while particular implementations and applications have been illustrated and described, it is to be understood that the disclosed implementations are not limited to the precise construction and components disclosed herein. Various modifications, changes and variations, which will be apparent to those skilled in the art, may be made in the arrangement, operation and details of the method and system disclosed herein without departing from the spirit and scope defined in the appended claims.

Although the foregoing text sets forth a detailed description of numerous different implementations, it should be understood that the legal scope of the invention is defined by the words of the claims set forth at the end of this patent. The detailed description is to be construed as exemplary only and does not describe every possible implementation, as describing every possible implementation would be impractical, if not impossible. One could implement numerous alternate configurations, using either current technology or technology developed after the filing date of this patent, which would still fall within the scope of the claims.

What is claimed is:

1. A seed sowing system for depositing seeds in a germination tray, comprising:
   a frame;
   a drum rotatably connected to the frame and rotatable about a longitudinal axis, the drum having a cylindrical peripheral wall and a hollow interior;
   a plurality of rows of apertures formed in the cylindrical peripheral wall and in fluid communication with the hollow interior, each row of the plurality of rows of apertures being parallel to the longitudinal axis;
   a hopper connected to the frame and configured to deliver seeds onto the cylindrical peripheral wall during operation;
   a vacuum configured to reduce pressure within the hollow interior of the drum so that the seeds from the hopper are temporarily held against the cylindrical peripheral wall at the plurality of rows of apertures in a plurality of rows of seeds;
   a light source configured to illuminate the plurality of rows of seeds one at a time as each row passes through an illumination region during operation;
   an optical detector positioned to receive light reflected by the plurality of rows of seeds when each row passes through the illumination region; and
   the light source comprising a laser configured to emit rays of light offset from the cylindrical peripheral wall of the drum so that the light source does not directly illuminate the cylindrical peripheral wall of the drum.

2. The seed sowing system of claim 1, comprising a conveyor configured to move the germination tray beneath the drum.

3. The seed sowing system of claim 2, the light source and the optical detector being arranged above the drum so that the light source and the optical detector are positioned on a side of the drum and the conveyor is positioned on an opposite side of the drum.

4. The seed sowing system of claim 1, the rays of light emitted by the laser are oriented at an angle relative to an optical detection path of the optical detector.

5. The seed sowing system of claim 4, the angle being equal to or greater than 5 degrees.

6. The seed sowing system of claim 1, the optical detector having a peak spectral sensitivity corresponding to a wavelength of light or a range of wavelengths of light emitted by the light source.

7. A seed sowing system for depositing seeds in a germination tray, comprising:
   a frame;
   a drum rotatably connected to the frame and rotatable about a longitudinal axis, the drum having a cylindrical peripheral wall and a hollow interior;
   a plurality of rows of apertures formed in the cylindrical peripheral wall and in fluid communication with the hollow interior, each row of the plurality of rows of apertures being parallel to the longitudinal axis;
   a hopper connected to the frame and configured to deliver seeds onto the cylindrical peripheral wall during operation;
   a vacuum configured to reduce pressure within the hollow interior of the drum so that the seeds from the hopper are temporarily held against the cylindrical peripheral wall at the plurality of rows of apertures in a plurality of rows of seeds;
   a light source configured to illuminate the plurality of rows of seeds one at a time as each row passes through an illumination region during operation;
   an optical detector positioned to receive light reflected by the plurality of rows of seeds when each row passes through the illumination region;
   a processor;
   the optical detector being configured to output seed signals to the processor based on the light reflected by each row of the plurality of rows of seeds as each row passes through the illumination region; and
   the processor being configured to process the seed signals to determine one of the following conditions for at least one of the plurality of apertures: (a) a presence of a single seed, (b) an absence of seeds, or (c) a presence of two or more seeds.

8. The seed sowing system of claim 7, comprising a display controllable by the processor to display, following a period of operation, information associated with at least one of: (a) a total number of counts of the presence of a single seed during the period of operation, (b) a total number of counts of the absence of seeds during the period of operation, or (c) a total number of counts of the presence of two or more seeds during the period of operation.

9. The seed sowing system of claim 7, comprising an encoder configured to output a position signal to the processor representative of a rotational position of the drum, wherein the only seed signals processed by the processor are the seed signals received by optical sensor when the drum occupies rotational positions corresponding to, respectively, each row of the plurality of rows of seeds passing through the illumination region.

10. A seed monitoring system comprising:
a rotatable drum having a cylindrical peripheral wall;
a plurality of apertures formed in the cylindrical peripheral wall and configured to hold seeds temporarily against the cylindrical peripheral wall with suction;
a directional light source configured to emit rays of light offset from the cylindrical peripheral wall so that the rays of light pass through an illumination region adjacent to the cylindrical peripheral wall; and
a detector positioned to receive the rays of light reflected by at least one of the seeds held on the cylindrical peripheral wall when the at least one of the seeds passes through the illumination region during rotation of the rotatable drum.

11. The seed monitoring system of claim 10, the rays of light emitted by the directional light source are oriented at an angle relative to a detection path of the detector.

12. The seed monitoring system of claim 10, comprising:
a processor;
the detector being configured to output seed signals to the processor based on the rays of light reflected by the at least one of the seeds; and
the processor being configured to process the seed signals to determine one of the following conditions for at least one of the plurality of apertures: (a) a presence of a single seed, (b) an absence of seeds, or (c) a presence of two or more seeds.

13. The seed monitoring system of claim 12, comprising a display controllable by the processor to display, following a period of operation, information associated with at least one of: (a) a total number of counts of the presence of a single seed during the period of operation, (b) a total number of counts of the absence of seeds during the period of operation, or (c) a total number of counts of the presence of two or more seeds during the period of operation.

14. The seed monitoring system of claim 10, comprising an encoder configured to output a position signal to the processor representative of a rotational position of the rotatable drum, wherein the only seed signals processed by the processor are the seed signals received by the detector when the rotatable drum occupies rotational positions corresponding to, respectively, the seeds passing through the illumination region.

15. A method of monitoring seeds within a seed sowing system having a rotatable drum rotatable about a longitudinal axis, a directional light source, a detector, a processor, and a plurality of apertures formed in the rotatable drum, the plurality of apertures being configured to pick up, carry, and release the seeds, the method comprising:
providing a laser to emit rays of light perpendicular to the longitudinal axis of the rotatable drum and offset from a cylindrical peripheral wall of the rotatable drum;
providing an optical detector to receive the rays of light reflected by the seeds carried by the rotatable drum;
transmitting seed signals to the processor based on the rays of light received by the optical detector; and
processing the seed signals with the processor to determine a condition of at least one of the plurality of apertures.

16. The method of claim 15, wherein processing the seed signals with the processor comprises determining one of the following conditions for the at least one of the plurality of apertures: (a) a presence of a single seed, (b) an absence of seeds, or (c) a presence of two or more seeds.

17. The method of claim 16, wherein positioning the laser comprises arranging the laser so that the rays of light are oriented at an angle relative to an optical detection path of the detector.

18. The method of claim 17, comprising, following a period of operation, displaying on a display information associated with at least one of a: (a) a total number of counts of the presence of a single seed during the period of operation, (b) a total number of counts of the absence of seeds during the period of operation, or (c) a total number of counts of the presence of two or more seeds during the period of operation.

19. The method of claim 18, comprising:
determining a rotational position of the rotatable drum with an encoder and outputting a position signal to the processor representative of the rotational position of the rotatable drum; and
wherein processing the seed signals with the processor comprises processing only the seed signals received by the optical detector when the rotatable drum occupies rotational positions corresponding to, respectively, the seeds passing through the illumination region.

\* \* \* \* \*